United States Patent [19]

Larkin et al.

[11] Patent Number: 5,109,046
[45] Date of Patent: Apr. 28, 1992

[54] LIQUID ORGANOTINTHIOALKANOL STABILIZER COMPOSITIONS AND VINYL HALIDE RESIN COMPOSITIONS CONTAINING THE SAME

[75] Inventors: William A. Larkin, Avon By the Sea; Robert C. Ringwood, Sewaren; Matthew T. Stershic, Somerset, all of N.J.

[73] Assignee: Atochem North America, Inc., Philadelphia, Pa.

[21] Appl. No.: 662,546

[22] Filed: Feb. 28, 1991

[51] Int. Cl.⁵ .......................... C08K 5/58; C08K 5/57
[52] U.S. Cl. ................................. 524/178; 524/180; 524/181; 524/182
[58] Field of Search ................. 524/180, 182, 181, 178

[56] References Cited

U.S. PATENT DOCUMENTS

| | | | |
|---|---|---|---|
| 3,507,827 | 4/1970 | Pollock | 524/180 |
| 3,715,333 | 2/1973 | Larkin | 524/181 |
| 4,059,562 | 11/1977 | Hoch et al. | 524/182 |
| 4,254,017 | 3/1981 | Dworkin et al. | 260/429.7 |

FOREIGN PATENT DOCUMENTS 0059614  9/1982  European Pat. Off. ............ 524/181

Primary Examiner—Paul R. Michl
Assistant Examiner—Tae H. Yoon
Attorney, Agent, or Firm—Stanley A. Marcus

[57] ABSTRACT

This invention relates to heat and light stabilizer compositions for vinyl halide resin compositions comprising organotinthioalkanol compounds that are stabilized against gelation and precipitation, to methods of preparing the stabilizer compositions, and to stabilized vinyl halide resin compositions.

31 Claims, 1 Drawing Sheet

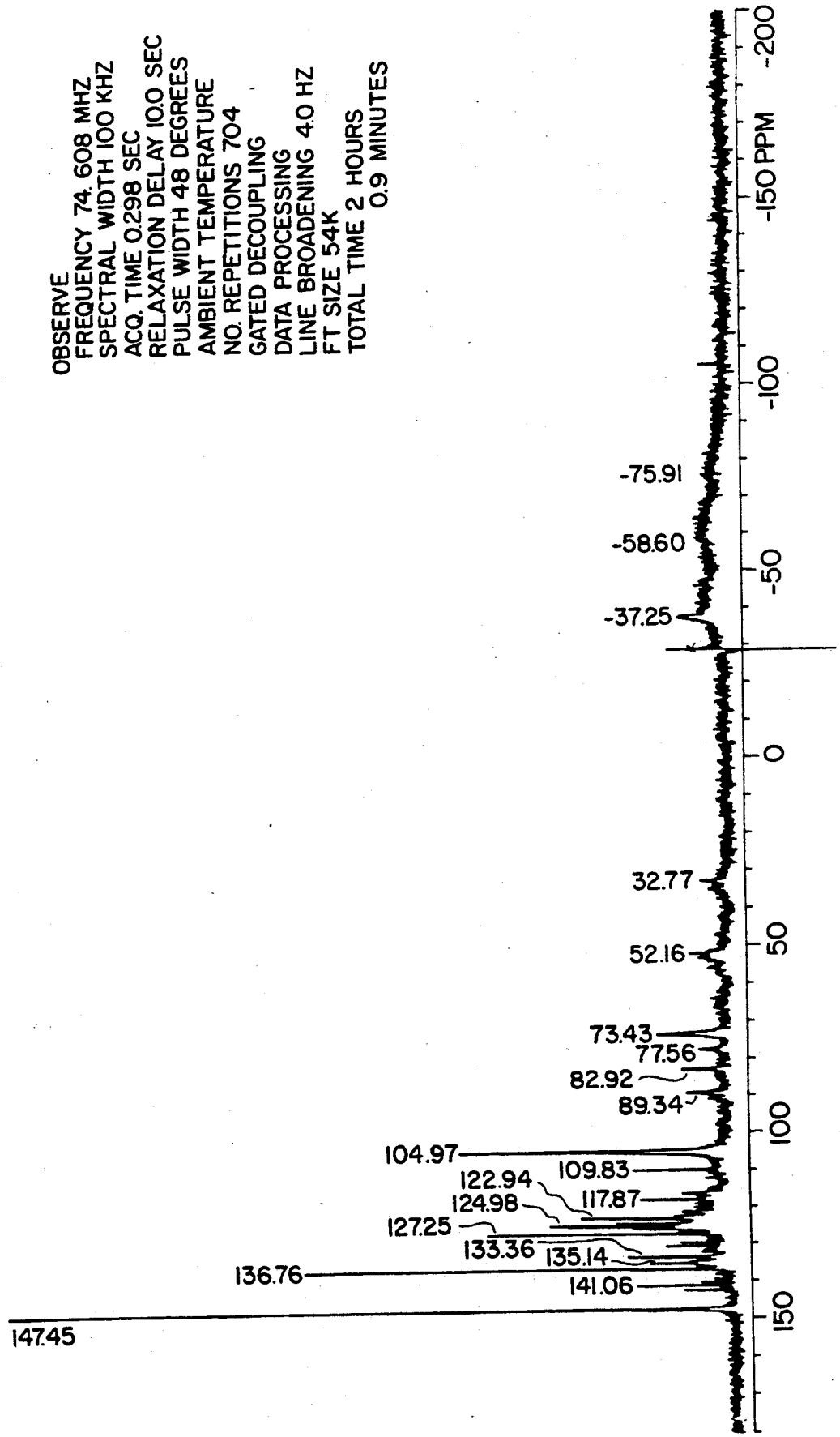

LIQUID ORGANOTINTHIOALKANOL STABILIZER COMPOSITIONS AND VINYL HALIDE RESIN COMPOSITIONS CONTAINING THE SAME

BACKGROUND OF THE INVENTION

The present invention relates to stabilizer compositions for vinyl halide resin compositions and, more particularly, to stabilizer compositions comprising organotinthioalkanol compounds that are stabilized against gelation and precipitation.

Vinyl halide resins and compositions containing vinyl halide resins are converted to useful articles by heating to soften or melt the resin, and then forming the desired product by thermoforming, i.e. converting the powdery resin composition to a molten mass which is then exposed to pressure to achieve the desired shape. The commercial processes for converting vinyl halide resins include calendering, in which the heated molten mass is converted to sheet or film utilizing a series of pressure generating rollers and take off rolls; extrusion, in which one or more screws convey the molten mass through a cylindrical barrel from which it is forced through shaping dies to form pipes, rods, sheet, profiles or tubes; extrusion blow molding, in which the molten mass is first extruded as a hollow tube called a parision which is then clamped in a mold chamber where compressed air is injected into the sealed tube to blow the item into the shape of the mold to form bottles, toys and other hollow items; and injection molding, in which the molten mass is pushed under high pressure into a mold cavity where it is subsequently chilled to form a solid article such as pipe fittings, electrical boxes, and other shapes.

Vinyl halide resin compositions are also used to coat paper and cloth, which may or may not be embossed. Additional processes for the conversion of vinyl halide resin compositions to useful articles include slush molding and fiber extrusion.

All of the processes for the conversion of vinyl halide resin compositions into useful articles require the use of heat to soften the vinyl halide resin so that it may be formed into the desired articles The heat may be generated by friction developed in the compound, as in extrusion, or externally applied heat such as the heated rolls of a calender. The heat required to soften the vinyl halide resin compositions varies with the compositions but is typically 165° C. to 210° C. Highly plasticized compounds such as calendered flexible sheets would use the lower temperature, while rigid or unplasticized vinyl halide resin compositions generally require the higher range of heat. Pipe, house siding, window profiles and rigid extruded sheet are normally formed at temperatures of 195° to 210° C.

It is well known that vinyl halide resins degrade in the presence of heat greater that 100° C. In fact some degradation occurs at even lower temperatures. Degradation of vinyl halide resins results in undesirable color changes and loss of physical properties. In extreme cases the vinyl halide resin compositions will turn black and become so brittle as to be unusable.

In order to protect the vinyl halide resin compositions against heat and light degradation, stabilizer materials are added. Compounds which have been used to stabilize vinyl halide resin compositions against heat degradation constitutes a broad range of materials and are well documented in the literature, e.g., the Encyclopedia of PVC 2nd Edition, 1986, Nass & Heiberger.

Typical stabilizers include lead salts and soaps, barium and cadmium soaps and phenolates, zinc soaps, antimony mercaptides, polyols, pentaerythritol, phosphites, epoxy compounds, amino compounds, magnesium compounds, calcium compounds and organotins.

As described in U.S. Pat. No. 3,919,168, it is well known in the art that organotin sulfur containing compounds, such as the organotin mercaptides, are among the most efficient (by weight) heat stabilizers for vinyl halide resins. U.S. Pat. No. 3,919,168 describes sulfur containing organotins, all of which are characterized by having at least one organic group bonded directly to tin through carbon and at least one sulfur atom bonded alone to tin or a residue of a sulfur containing group such as a mercaptan, or a mercaptoester bonded to tin through sulfur. Both sulfur alone bonded to the organotin and the residue of a sulfur containing moiety may be bonded to the same organotin moiety.

Liquid organotin compounds containing thioalkanol groups bonded to tin through sulfur are also known to be effective stabilizers for vinyl halide resin compositions. U.S. Pat. Nos. 4,059,562 and 4,254,017 disclose organotin compounds which contain thioalkanol groups bonded to tin through sulfur, and disclose their use as heat stabilizing compounds for vinyl halide resins. Organotin ethanolmercaptides represent one class of organotinthioalkanols.

While organotinthioalkanols are highly effective stabilizers for vinyl halide resin compositions, they have several serious shortcomings which have prevented widespread production and commercialization. The most serious deficiency of this class of compounds and compositions is their poor storage stability. Upon standing, in most instances even for a few days, the organotinthioalkanols form viscous, gelatinous mixtures and frequently precipitation occurs. The resultant non-homogenous compositions are difficult to handle, i.e., to pump and meter and, as a result, it is not possible to achieve the uniformity required from batch to batch in a vinyl resin composition. Further the solid precipitate must be filtered out and discarded as waste, which results in a loss of 10% to 20% of this costly product.

An additional serious deficiency of organotinthioalkanols is evident in manufacture. The viscous materials are very difficult to stir and mix and precipitates block transfer lines and contaminate storage vessels. Extra steps must be taken after each production batch to clean out reactors, transfer lines, filters and storage vessels.

As described in U.S. Pat. No. 4,059,562, Hoch et al. propose to solve the viscosity and precipitation problems of organotinthioalkanols by dissolving the organotin in 10% to 60% by weight (of the organotin) of a liquid alcohol component comprising a glycol having 2 to 10 carbon atoms and 0.1 to 1% by weight (of the organotin) of an alkyl acid phosphate. See col. 4, lines 48-62.

Hoch et al. at col. 3, lines 66- 68 and col. 4, lines 1-3, disclose that particularly good results have been obtained when the liquid alcohol component of the stabilizer system contained from 50 to 100% by weight of hexylene glycol and up to 50% by weight of one or more straight chain and or branched chain monohydric alcohols having 8 to 15 carbon atoms.

Employing relatively large amounts of water miscible solvents, 10% to 60% based on the weight of the organotinthioalkanol, as proposed by Hoch et al., is undesirable in the majority of applications for vinyl halide resin stabilization since water resistance of the vinyl halide resin compositions is decreased in the presence of such materials.

It is known in the art that precipitation in organotin mercaptoacid esters can be eliminated by employing a stoichiometric excess of the organotin chloride during the reaction with the mercaptoacid ester. It is also known, as described in U.S. Pat. No. 3,715,333 to Larkin, to use mixtures of organotin chlorides and organotin mercaptoacetates or mercaptides as stabilizers for vinyl halide resins. However, organotin chlorides alone do not eliminate the precipitation problem encountered with conventional organotinthioalkanol stabilizers.

Thus, there is a need for shelf stable organotinthioalkanol stabilizer compositions that are stabilized against gelation and precipitation.

BRIEF DESCRIPTION OF THE DRAWING

The Figure is a plot of the NMR ($^{119}$Sn) spectrum of an organotinthioalkanol stabilizer composition containing bound chlorine and free mercaptan.

SUMMARY OF THE INVENTION

It has now been found that organotinthioalkanol stabilizer compositions with excellent shelf stability can be obtained by incorporating about 0.1% to about 10% by weight of free mercaptan in combination with 0 to 10% by weight of bound chlorine into the organotinthioalkanol stabilizer compositions. Such compositions have been shown to be free of gelation, viscosity increase and precipitation after many weeks of storage and after repeated cycling from $-20°$ C. to $25°$ C.

Vinyl halide resin compositions stabilized with these organotinthioalkanol stabilizer compositions are also included in this invention.

The invention also provides an improved process for the manufacture of organotinthioalkanol stabilizer compositions, the improvement being characterized by the formation of low viscosity, gelation and precipitate free organotinthioalkanol stabilizers which are easy to filter and handle.

DETAILED DESCRIPTION OF THE PREFERRED EMBODIMENTS

We have now found that liquid organotinthioalkanol stabilizer compositions having good shelf stability, i.e., substantially free of gelation and precipitate, and excellent stabilization properties for vinyl halide resin compositions can be obtained by having present in the organotinthioalkanol compositions about 0.1% to about 10%, preferably from about 0.1% to about 5%, of free mercaptans and from 0 to about 10.0%, preferably from about 0.1% to about 10.0% and most preferably from about 0.1% to about 2.0%, of bound chlorine. The aforementioned percentages are by weight of the total stabilizer composition.

The incorporation of the free mercaptan without the incorporation of the bound chlorine is somewhat effective to protect against degradation of the organotinthioalkanol during storage. The incorporation of chlorine bonded to the stabilizer composition without the addition of free mercaptan has been shown to form two separated liquid phases, a dense, viscous lower phase and a less viscous upper phase. Preferred stabilizer compositions contain at least 0.1% by weight of free mercaptan and at least 0.1% by weight of the bound chlorine.

Selected organotinthioalkanol stabilizer compositions of the present invention containing bound chlorine and free mercaptan may be characterized by the presence of about 3% to about 35% by weight of mercapto sulfur, about 0.1% to about 10% by weight of bound chlorine, about 0.1% to about 10% by weight of a free mercaptan compound, and about 16% to about 46% by weight of tin.

Organotin compounds and compositions containing at least one (1) thioalkanol group bonded to the organotin which are useful in this invention have the structural formula

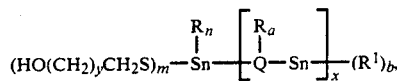

wherein:

R, independently, represents an alkyl group having 1 to 12 carbon atoms or a carboalkoxyhydrocarbyl or a ketohydrocarbyl group having at least four carbon atoms, said groups being bonded to tin through carbon;

y represents 1 or 2;

$R^1$, independently, represents —SCH$_2$CH$_2$OH, —SCH$_2$—CH—(OH)—CH$_3$, —SCH$_2$COOR, —SCH$_2$CH$_2$O—COR$^2$, —SR$^2$, —OOCR$^2$, or —OOCR$^3$—COOR$^2$;

$R^2$ represents an alkyl on alkaryl group having 6 to 18 carbon atoms;

$R^3$ represents —CH=CH—; or —CH$_2$—R$^{12}$—CH$_2$—, wherein $R^{12}$ represents an alkylene group having 2 to 6 carbon atoms;

Q represents oxygen or sulfur;

a, b, m and n each represents 1 or 2;

x represents 0 to 4; and when x is 0, m+n+b=4 and when x is 1, m+n=3 and a+b=3 and when x is greater than 1, m+n=3 and one of a+b=3 and the balance of a=2. The mercaptoalkanol residue in these compounds generally comprises about 3% to about 67% by weight of the organotinthioalkanol compound.

The structural formula used above to identify the organotinthioalkanols as well as the compounds listed below all suggest that these are discrete molecules. It is, however, well known that organotin "compounds" which contain at least two tin atoms bonded to each other through sulfur or oxygen are not discrete molecules, but three or more separate compounds existing in a dynamic equilibrium as a result of redistribution, thus these materials are more properly identified as compositions.

While a single structural formula may be used to describe such "bridged" materials as a form of short hand for ease of discussion and the chemical analysis for tin, carbon, oxygen, hydrogen, chlorine, and sulfur will correspond to that which can be shown to be theoretically present in such a single structure, it is necessary to use other analytical techniques to identify the various molecules present in the composition. Tin and carbon NMR are preferred techniques to characterize organotin compositions of this invention. A description of NMR or Nuclear Magnetic Resonance Spectroscopy, may be found in many literature sources, one of which is the Encyclopedia of Chemical Technology, 3rd Edition, Vol. II, Wiley.

Examples of organotinthioalkanols representative of compounds and compositions within the above definition include mono-methyltin tris (2-hydroxyethylmercaptide), mono-butyltin tris (3-hydroxypropylmercaptide), monooctyltin mono (isooctylthioglycolate) di (2-hydroxyethylmercaptide), mono-butyltin di (2-hydroxyethylmercaptide) (dodecylmercaptide), mono-methyltin di(3-hydroxypropylmercaptide) (oleylmercaptide), di-methyltin (2-hydroxyethyl mercaptide) (laurylmercaptide), di-butyltin (2-hydroxyethylmercaptide) (iso-octylmercaptoacetate), di-butyltin (2-hydroxyethylmercaptide) (oleylmercaptoalkanoate), mono-butyltin (2-hydroxyethylmercaptide) dichloride, mono-butyltin bis (2-hydroxyethylmercaptide) chloride, di-methyltin (2-hydroxyethylmercaptide) chloride, bis [mono-butyltin (dodecylmercaptide) (2-hydroxyethylmercaptide)] sulfide, [mono-butylti (dodecylmercaptide) (2-hydroxyethylmercaptide)] [mono-butyltin (2-hydroxy-ethylmercaptide)(chloride)] sulfide, [mono-butyltin(laurate) (2-hydroxyethylmercaptide)] [di-butyltin (2-hydroxyethylmercaptide)] sulfide, and bis [mono-butyltin (dodecylmercaptide) (2-hydroxyethylmercaptide)] oxide. Preferred organotinthioalkanol stabilizer compounds and compositions are bis [mono-butyltin (dodecylmercaptide) (2-hydroxyethylmercaptide)] sulfide, bis[mono-methyltin (2-hydroxyethylmercaptide) (chloride)] sulfide, [mono-butyltin(dodecylmercaptide) (2-hydroxyethylmercaptide)] [mono-butyltin (2-hydroxyethylmercaptide)(chloride)] sulfide, mono-octyltin mono(isooctylthioglycolate) di(2-hydroxyethylmercaptide), mono-methyltin di(3-hydroxypropylmercaptide)(oleylmercaptide), [mono-butyltin(behenate) (2-hydroxyethylmercaptide)] [dibutyltin(2-hydroxyethylmercaptide)] sulfide, bis[mono-methyltin (dodecylmercaptide)(2-hydroxyethylmercaptide)] sulfide, [(mono-butyltin bis(tridecylmercaptide) dibutyltin 2-hydroxyethylmercaptide)] sulfide, and bis(-dimethyltin 2-hydroxyethylmercaptide) sulfide.

Other organotinthioalkanol compounds suitable for use in the present invention, and their methods of preparation, are described in U.S. Pat. Nos. 4,059,562 and 4,254,017, both of which are hereby incorporated by reference.

In addition to the organotinthioalkanol compounds described above, other organotin compounds may be added to the organotinthioalkanol stabilizer compositions of the present invention. Included within the class of useful organotin compounds are those containing one or more tetravalent tin atoms each of which have at least one direct tin-to-carbon bond. Such compounds are described in U.S. patents and other references. The stabilizer used is preferably substantially non-volatile at ordinary temperatures, namely, 180° C., and dispersible in the selected vinyl resin, that is, compatible to the extent that it may be compounded with the resin in compounding operations which are used in this industry.

A useful class of such tin-containing heat stabilizers are compounds containing one or more tetravalent tin atoms which each have at least one direct tin-to-sulfur or tin-to-oxygen bond, that is which contain a group:

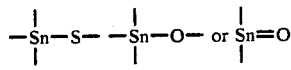

Examples of such compounds with tin-to-sulfur bonds are described in U.S. Pat. No. 3,764,571, issued to Jennings, and examples of compounds with tin-to-oxygen bonds are described in U.S. Pat. No. 3,167,527, to Hechenbleikner et al., both of which are hereby incorporated by reference.

Organotin compounds include those containing one or more tetravalent tin atoms having at least one direct tin to carbon bond and wherein the remaining valences of the tin atom are satisfied by bonds to either oxygen, sulfur or a residue resulting from removal of the hydrogen atom from the sulfur atom of a mercaptan, mercaptoacid, mercaptoacid ester or mercaptoalcohol ester or a residue resulting from removal of the hydrogen atom from the oxygen atom of a carboxylic acid or alcohol or halogen acid with the provision that at least one valence site is satisfied with oxygen or sulfur or mixture thereof. Organotin compounds include methyltin mercpatide, butyltin mercaptide, octyltin mercaptide, ester tin mercaptide, and the reaction product of an organotin halide with alkaline metal sulfide and mercaptide, mercaptoacid esters, or mercaptoalcohol esters or mixtures thereof. Other tin compounds include organotin mercaptides, halogen containing sulfur or oxygen bridged organotin mercaptides, alkyltin carboxylates, and organotin alkoxides. The organotin compounds include an organotin chloride/organotin mcrcaptide combination or an alkyl chlorotin carboxylate.

These organotin compounds, like the organotinthioalkanols, are known to undergo redistribution in the presence of oxygen or sulfur bridged organotin compounds.

The term bound chlorine in the present invention means that a chlorine atom is covalently bonded directly to the tin atom of one or more of the following compounds: the organotinthioalkanol; the organotin chloride; or an organotin compound formed during the redistribution of the organotinthioalkanol and the tin of the organotin chloride. If organotin compounds other than organotinthioalkanols are also added to the stabilizer composition, then the chlorine atom may be bonded to the tin atom of these compounds as well. The bound chlorine content of the stabilizer can be measured with conventional analytical procedures.

The bound chlorine may be incorporated into the organotinthioalkanol stabilizer compositions, by adding an organotin chloride or the organotin chlorides may be generated "in-situ" during the manufacture of the organotinthioalkanol as described below. When added to the organotinthioalkanol compounds or compositions, they may react in whole or in part through redistribution reactions to form organotin (thioalkanol) chlorides or organotin (thioalkanol)(mercaptide) chlorides or other organotin compounds having at least one chlorine bonded to the organotin.

When the organotin chlorides are to be formed "in situ", this may be accomplished by neutralizing less than the total amount of chloride available in the organotin chloride raw material or intermediate and reacting less than the stoichiometric amounts of mercaptans, sulfide or oxides and mercaptoalkanol needed to satisfy all valence bonds not satisfied by organotin groups bonded to tin through carbon. In other words, there is a stoichiometric excess of the organotin chloride that remains with the organotinthioalkanol reaction product and it is used as the bound chlorine.

Organotin chlorides useful in this invention include organotin compounds having 1 or 2 organic groups bonded to the tin atom through carbon and at least one chloride atom bonded directly to tin. These organotin chlorides can be represented by the structural formula

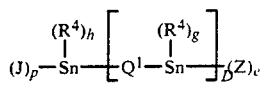

wherein $R^4$, independently, represents an alkyl group having 1 to 12 carbon atoms or a carboalkoxyhydrocarbyl or a ketohydrocarbyl group having at least four carbon atoms, said groups being bonded to tin through carbon;

$Q^1$ represents oxygen or sulfur;

J and Z each, independently, represent chlorine, $-SCH_2CH_2OH$, $-SCH_2CH_2CH_2OH$, $-SCH_2-CH-(OH)-CH_3$, $-SCH_2COOR^5$, $-SCH_2C-H_2O-COR^5$, $-SR^5$, $-OOCR^5$, or $-OOCR^6-COOR^5$, provided that at least one of J and Z is chlorine;

$R^5$ represents an alkyl or alkaryl group having 1 to 18 carbon atoms;

$R^6$ represents $-CH=CH-$ or $-CH_2R^7-CH_2-$;

$R^7$ represents an alkylene group having 2 to 6 carbon atoms;

D represents 0 to 4;

g, h, p and e each represent 1 or 2; and when D is 0, $h+p+e=4$, and when D is 1, $h+p=3$ and $g+e=3$, and when D is greater than 1, $h+p=3$, one of $g+e=3$ and the balance of $g=2$.

Specific organotin chlorides which may be added to the organotinthioalkanols are selected from the group comprising di-organotin chlorides, mono-organotin chlorides, mixtures of mono/diorganotin chlorides and organotin chlorides in which at least one valence site is satisfied by the residue of a mercaptan, mercaptoalkanol, mercapto-acid ester, mercaptoalkanol ester, carboxylic acid, carboxylic acid ester or an hydroxide, oxide or sulfide. Preferred organotin chlorides which may be added to the organotinthioalkanols are monomethyltintrichloride, monobutyltintrichloride, monooctyltin trichloride, dibutyltin (chloride)(hydroxide), bis (mono-butyltin dichloride) oxide and bis (mono-butyl tin dichloride) sulfide.

The sulfur containing compounds useful as free mercaptans in this invention include any compound containing at least one mercapto group, $-SH$, capable of interacting with organotin bound chlorine to effect stabilization of organotinthioalkanols. Suitable mercaptans can be represented by the following structural formulas $R^8SH$; $HS-R^9-SH$;

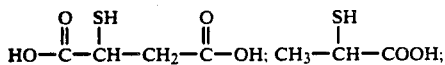

or $R^{11}(SH)_t$, wherein $R^8$ represents an alkyl or alkaryl group of 8 to 20 carbon atoms, the residue of a monocarboxylic acid having an alkylene group of 1 to 3 carbon atoms, the residue of a monocarboxylic acid ester having 2 to 3 carbon atoms in the acid portion and 1 to 20 carbon atoms in the alcohol portion, the residue of a mercaptoalkanol ester having 2 to 6 carbon atoms in the alcohol portion and 2 to 30 carbon atoms in the acid portion of the ester, or the residue of a mercaptoalkanol having 2 to 20 carbon atoms;

$R^9$ represents $-CH_2-R^{10}-CH_2-$;

$R^{10}$ represents an alkylene group of 8 to 20 carbon atoms or an aryl group of 6 to 20 carbon atoms;

$R^{11}$ represents a substituted or unsubstituted, saturated or unsaturated cyclic, polycyclic, oligomeric or polymeric hydrocarbyl radical having 2 or more hydrogens substituted by mercapto ($-SH$) groups; and t represents 2 to 10.

Preferred sulfur containing compounds include mercaptoalkanols, mercaptoalkanol esters, mercapto acids, mercaptoacid esters, thiolactic acid, thiomalic acid, thioglycolic acid, isooctylmercaptoacetate, 2-ethylhexyl mercaptoacetate, alkylmercaptans, dodecyl mercaptan, benzyl mercaptan, and hydroxy mercaptan. Most preferred sulfur containing compounds are mercapto acid esters and mercapto alkanol esters.

The organotinthioalkanol stabilizer compositions may be used alone or in mixture with organotin stabilizers which do not contain thioalkanol residue groups such as organotin mercaptides, organotin sulfides, organotin mercaptoacidesters, organotin mercaptoalkanolesters and organotin carboxylates.

Additionally, it may be desirable to provide the organotinthioalkanol stabilizers of this invention in a diluted form to enhance ease of handling, dispersion in the vinyl halide resin composition and to improve accuracy of metering. Any of the diluent materials normally used with organotin stabilizers may be used provided they are compatible with the organotinthioalkanol stabilizer composition. Typical diluents include organic esters and mineral oils.

The organotinthioalkanol stabilizer compositions of this invention are useful as heat and light stabilizers for vinyl halide resin compositions. They are particularly effective in controlling the initial and early color of vinyl halide resin compositions when exposed to elevated temperatures, and will not adversely affect processability of such vinyl halide resin compositions. The vinyl halide resin compositions of this invention contain at least about 0.1%, and preferably from about 0.1% to about 5%, by weight (of the vinyl halide resin) of the stabilizer composition.

The vinyl halide resins that may be present in the vinyl halide resin compositions include homopolymer vinyl halides such as polyvinyl chloride, polyvinylidene chloride, chlorinated polyvinyl chloride and copolymers formed by the polymerization of a vinyl halide monomer with up to 40% of a comonomer such as vinyl acetate, vinyl butyrate, vinylidene chloride, propylene, methylmethacrylate and the like. The invention also includes stabilized vinyl halide resins compositions containing other polymers such as chlorinated polyethylene; terpolymers of acrylonitrile, butadiene, styrene; terpolymers of methylmethacrylate, butadiene, styrene polyacrylate resins; polymethylmethacylate resins and terpolymer of alkyl acrylate, methylmethacrylate, butadiene. Such polymeric add-itives function primarily as impact strength improvers and processing aids.

In addition to the above mentioned polymeric additives, vinyl halide resin compositions may contain plasticizers, lubricants, pigments, fillers, dyes, extenders, antistats, antioxidants, chelators and UV absorbers.

The compounds and compositions of this invention can be prepared using one or more of the procedures found in the following Examples. The reactions can be carried out within a wide range of temperatures, i.e., from ambient temperatures to 150° C. Preferably, the reactions are carried out at 25° C. to about 95° C. in an aqueous medium to produce the organotinthioalkanol composition.

EXAMPLE 1

Preparation of bis [monobutyltin (dodecylmercaptide) (2-hydroxyethylmercaptide)] sulfide A one liter, three necked flask with bottom drain was equipped with a mechanical stirrer and thermometer.

To the flask was added 225.48 grams of water, 162.19 grams of dodeylmercaptan and 63.01 grams of mercaptoethanol. The mixture was stirred and 225.98 grams of mono-butyltin trichloride was added and the temperature increased from 22° C. to 48° C. Following the mono-butyltin trichloride addition, 311.11 grams of 20% by weight sodium hydroxide in water was added gradually in such a manner that the temperature did not rise above 54° C. The mixture was then heated and stirred at 55° C. for 30 minutes after which, 53.2 grams of sodium sulfide flake (60% Na2S) was added and the mixture heated to 84° C. and held there while stirring for 30 minutes. At this point, the pH was determined to be 4.15. The pH was adjusted to 4.75 with 20% aqueous sodium hydroxide solution. Following pH adjustment, agitation was stopped and two phases separated. The lower phase was the product phase which was split off to a product holding vessel.

After the product phase was split off, 10 drops of a surfactant was added to the aqueous phase, stirred and then allowed to settle for 30 minutes. A small amount of product was recovered from the aqueous phase. It was added to the product phase.

The aqueous phase was drained from the reaction flask and discarded. The product phase was poured back into the reaction flask, heated to 90° C. and vacuum stripped at 5 mm pressure until no more water came off overhead. The vacuum was then broken, 3 grams of filter aid was added to the product and the mixture was polish filtered to yield a clear yellow product. Analysis of the product was completed with the following results:

|  | Calculated | Found |
| --- | --- | --- |
| Tin. Wt % | 24.94 | 24.94 |
| Mercapto sulfur Wt % | 19.32 | 19.32 |
| Chlorine. Wt % | 0 | None |
| Color | — | 3 |
| Specific Gravity | — | 1.5486 |

Tin NMR showed the composition to be a mixture of 20 organotin species with 6 major species and 14 minor species.

The composition produced in this example became cloudy with gelation and precipitation beginning to develop within 7 days of production at ambient temperature storage.

EXAMPLE 2

Production of bis [mono-butyltin(dodecylmercaptide) (2-hydroxyethylmercaptide)] sulfide A production size batch of several thousand pounds of bis[mono-butyltin(dodecylmercaptide)(2-hydroxyethymercaptide)] sulfide was produced following the procedure disclosed in example 1. Precipitation formed in the product necessitating filtration. The product was heated to 50° C. and filtered with a loss of 13% by weight. Following filtration the product was analyzed with the following results:

|  | Calculated | Found |
| --- | --- | --- |
| Tin, Wt % | 24.94 | 25.0 |
| Mercapto sulfur Wt % | 19.32 | 18.6 |
| Chlorine. Wt % | 0.0 | 0.97 |
| Color | — | 3 |

The product of this example became cloudy with gelation and precipitation in less than 7 days.

EXAMPLE 3

Preparation of bis [mono-butyltin(dodecylmercaptide) (2-hydroxyethylmercaptide)] sulfide containing chlorine bonded to organotin from the initial organotin chlorides charge A clean dry 1-liter, bottom drain, 4-necked flask is equipped with a mechanical stirrer, thermometer, and addition funnel. To the flask is added distilled water (225.70g), followed by n-dodecylmercaptan (161.92g, 0.80 mol) and 2-mercaptoethanol (62.50g, 0.80 mol). This mixture is then agitated and monobutyltin trichloride (225.73g, 0.80 mol) is added. An exotherm occurs raising the temperature from room temperature (22° C.) to approximately 46° C. After this mixture is stirred for 5 minutes, 20% sodium hydroxide solution (300g) is added dropwise via the addition funnel. The addition rate is kept such that the temperature of the reaction mixture remains below 54° C. When the addition is complete, the mixture is stirred for 30 minutes at 57° C. Following this reaction time, sodium sulfide (60% Na2S) (52.04g, 0.40 mol) is added and the mixture heated to 85° C. for 30 minutes. At this point, the pH of the reaction mixture is taken and adjusted to pH 4.75 using 20% sodium hydroxide solution (16.0g). After the pH is obtained, agitation is stopped and the two phases are allowed to split. After setting for 15 minutes, the product phase (lower) is split off. The upper aqueous phase is removed and then the product is brought back into the flask. Next, 2-ethylhexylmercaptoacetate (7.50g, 0.037 mol) is added to the product and the mixture stirred. Vacuum (15 mm Hg) is then pulled on the reactor while it is slowly heated to 95° C. to remove residual water. When no more water is observed coming from the reaction vessel, heating is stopped and the product cooled to 50° C. The vacuum is then broken and filter aid (approx 3g) is added and the mixture stirred for an additional 5 minutes. The material is then polish filtered to give a clear yellow product.

The product of this example contains 2% unreacted or free 2-ethylhexylmercaptoacetate and 1% bound chlorine.

EXAMPLE 4

Preparation of monobutyltin tris (3-mercaptopropanol) containing chlorine bonded to organotin from the initial organotin charge A clean dry 1-liter, bottom drain, 4-necked flask is equipped with a mechanical stirrer, thermometer, and addition funnel. To the flask is added distilled water (50.00g), followed by 3-mercaptopropanol (221.18g, 2.4 mol). This solution is agitated and monobutyltin trichloride (225.73g, 0.80 mol) is added to the mixture. The solution is stirred for 5 minutes, and then 20% sodium hydroxide (450g) is added dropwise, via the addition funnel, keeping the reaction temperature below 55° C. At this point, the mixture is heated at 55° C. for 30 minute and then the pH is adjusted to 6.5 using 20% sodium hydroxide (25.0g). Agitation is then stopped and the phases are split. The lower phase is the aqueous phase, and this is drained from the flask. 2-ethylhexyl-mercapto-acetate (9.00g, 0.044 mol) is then added to the product and the mixture is stirred. Vacuum (15 mm Hg) is then pulled on the reactor while it is heated to 90° C. to remove the residual water. When no more water is observed coming from the reaction vessel, heating is stopped and the product cooled to 50° C. The vacuum is then broken and filter aid (approx 3g) is added and the mixture stirred for an additional 5 minutes. The material is then polish filtered to give the product.

The product of this Example contains 2% free 2-ethylhexylmercaptoacetate and 1% bound chlorine.

Examples 1,2,3 and 4 use organotin chlorides as the raw material in the synthesis of the organotinthioalkanols. It is understood that organotin oxides and organotin hydroxides or mixed organotin (oxides) chlorides and organotin (hydroxides) chlorides can also be used as the raw materials, in which instance it is not necessary to employ sodium hydroxide or another basic material to neutralize the chloride ions.

EXAMPLES 5-14

The objective of the work performed in Examples 5-15, was to eliminate the haze, gelatinous matter and precipitates in bis [mono-butyltin(dodecylmercaptide)(2-hydroxyethylmercaptide)] sulfide and to stabilize the composition against degradation during storage.

To equal aliquots of product produced in Example 2, the following additions were incorporated at the weight percent noted after heating the product of Example 2 to 50° C. The appearance after storage for the indicated times, with and without freeze/thaw cycles is also noted.

The calculated analytical values for the product of Example 2, to which was added 2% by weight of 2-ethyhexyl mercaptoacetate and 1% by weight of mono-butyltin trichloride are as follows:

Tin, Wt%—24.9%
Mercapto Sulfur, Wt%—20.15%
Chlorine, Wt %—0.36%

A $^{119}$Sn NMR spectrum of the stabilizer composition containing the product of Example 2 to which was added 1% by weight of mono-butyltin trichloride plus 2% by weight of 2-ethylhexyl mercapto acetate is shown in the Figure. The reference for this spectrum was tetramethyl tin. The abscissa of the spectrum represents the chemical shifts (ppm) of the organotin species, while the ordinate shows the relative intensities of these species.

TABLE I

| EXAMPLE # | PRODUCT OF | ADDITION | 2 HOURS | 6 HOURS | 1 CYCLE |
|---|---|---|---|---|---|
| 5 | EXAMPLE #2 | NONE | C | C | C |
| 6 | " | 1 WGT % MBTTC | SLIGHT HAZE | SLIGHT HAZE | C |
| 7 | " | 3 WGT % MBTTC | SLIGHT HAZE 2 PHASES | SLIGHT HAZE 2 PHASES | C |
| 8 | " | 2 WGT % DOCEYL-MERCAPTAN | C | SLIGHT HAZE | SLIGHT HAZE WITH PPT |
| 9 | " | 3 WGT % DOCEYL-MERCAPTAN | C | C | C |
| 10 | " | 2 WGT % 2-ETHYLHEXYL-MERCAPTOACETATE | C | C | C |
| 11 | " | 3 WGT % 2-ETHYLHEXYL MERCAPTOACETATE | C | C | C |
| 12 | " | 3 WGT % MONO-BUTYLTIN TRIS 2-ETHYL-HEXANOATE | C | C | C |
| 13 | " | 1 WGT % MBTTC + 2 WGT % DODECYL-MERCAPTAN | C | C | C |
| 14 | " | 1 WGT % MBTTC + 2 WGT % 2-ETHYLHEXYL MERCAPTOACETATE | C | C | C |

| EXAMPLE # | 2 CYCLES | 3 CYCLES | 6 WEEKS |
|---|---|---|---|
| 5 | C | C | HAZE WITH PPT |
| 6 | C | C | HAZE WITH PPT |
| 7 | C | C | VERY HAZY WITH PPT |
| 8 | SLIGHT HAZE WITH PPT | SLIGHT HAZE WITH PPT | VERY HAZY WITH PPT |
| 9 | C | C | SLIGHT HAZE |
| 10 | C | C | SLIGHT PPT |
| 11 | C | C | SLIGHT HAZE |
| 12 | C | C | SLIGHT PPT |
| 13 | C | C | SLIGHT PPT |

TABLE I-continued

| | | | |
|---|---|---|---|
| 14 | C | C | CLEAR |

NOTES:
(1) "Cycle" refers to freeze/thaw cycles which consist of heating the sample to 60° C. in an oven for four (4) hours followed by freezing the sample in a chest freezer at minus 20° C. for 16 hours. Samples from the freeze/thaw cycle were returned to room temperature, approximately 22° C., prior to evaluating for appearance.
(2) MBTTC is mono-butyltin trichloride.
(3) C means that the product appears clear.

It is apparent from comparing the results of Example with Examples 5-12, that it is the combination of free mercaptan and bound chlorine which yields clear, liquid shelf stable organotinthioalkanol compounds and compositions. The results of Example 13 when compared with Example 9 indicate that in this instance the concentration of free dodecylmercaptan should be increased to 3% weight of the organotinthioalkanol to achieve a clear, liquid shelf stable organotinalkanol composition.

EXAMPLE -

Heat stability testing was carried out using a rheometer designed to heat and mix a stabilized vinyl halide resin composition by use of counter rotating rotors positioned in a bowl for containing the resin composition. The color of the charge is determined at 2 minute intervals by removing a small quantity of the molten mass, forming into a "button" by pressing and measuring the "Yellowness Index" on a MacBeth colorimeter, the higher the Yellowness Index number, the greater the yellowness of the sample. Samples with greater than approximately 25 Yellowness Index are already so colored as to be unusable in such products as PVC house siding.

In this example, the charge weight of the stabilized PVC compound was 62 grams of compound which was charged to the rheometer bowl; the rotor speed was 75 rpm and temperature was maintained at 190° C. Results of this test are shown in Table II. In each case, the stabilized PVC composition consisted of (weight parts):

PVC resin, Geon 103 EP—100
Titanium dioxide—1
Acrylic impact modifier—5
Acrylic process aid—1
Paraffin wax, 165° MP°0.9
Calcium stearate—0.8
Stabilizer—0.9

TABLE II

| | Yellowness Index | | | | | | |
|---|---|---|---|---|---|---|---|
| | Time in Minutes | | | | | | |
| Sample | 2 | 4 | 6 | 10 | 15 | 20 | 25 |
| A. Control | 6.9 | 9.9 | 12.4 | 14.7 | 21.7 | 29.2 | 36 |
| B. Product of Example 14 | 6.2 | 5.4 | 6.3 | 7.5 | 8.6 | 11.6 | 17.7 |

Control=(dibutyltinisooctylmercaptoacetate)(monobutyltin bis(isooctylmercaptoacetate) sulfide.

Table II shows that the PVC resin compositions containing the organotinthioalkanol stabilizers with bound chlorine and free mercaptan have superior early color and color hold than the resin compositions containing the comparative commercial stabilizer.

The Examples shown above are not considered to limit the invention, but are only illustrative of the stabilizer compositions of the present invention.

We claim:

1. In an organotinthioalkanol stabilizer composition, the improvement which comprises the presence of: 0.1% to about 10% by weight of total stabilizer composition of bound chlorine and about 0.1% to about 10% by weight of total stabilizer composition of a free mercaptan, whereby gelation and precipitation of the organotinthioalkanol stabilizer composition are substantially eliminated.

2. A stabilizer composition according to claim 1 comprising about 0.1% to about 2.0% by weight of total stabilizer composition of bound chlorine and about 0.1% to about 5.0% by weight of total stabilizer composition of the free mercaptan.

3. A stabilizer composition according to claim 2 wherein the bound chlorine is incorporated into the composition by adding an organotin chloride or is present in the composition as an unreacted organotin chloride remaining after the formation of the organotinthioalkanol stabilizer.

4. A stabilizer composition according to claim 3 wherein the free mercaptan is selected form the group consisting of alkyl mercaptans, mercaptoacids, mercapto alkanols, mercaptoacid esters, mercaptoalkanol esters and mixtures thereof.

5. A stabilizer composition according to claim 4 wherein the organotin chloride comprises monobutyltin trichloride and the free mercaptan comprises 2-ethylhexyl mercapto acetate.

6. A stabilizer composition according to claim 4 wherein the bound chlorine is bonded to at least one of the tin of the organotinthioalkanol stabilizer, the tin of an organotin compound formed during the redistribution of the organotinthioalkanol and the tin of the organotin chloride, or the tin of the organotin chloride.

7. A stabilizer composition according to claim 1 having the NMR spectrum shown in the Figure.

8. A resin composition comprising:
at least one vinyl halide resin and
the organotinthioalkanol composition of claim 1.

9. A polyvinyl chloride pipe stabilized with the organotin thioalkanol composition of claim 1.

10. A polyvinyl chloride injection molded article stabilized with the organotinthioalkanol composition of claim 1.

11. A polyvinyl chloride house siding product stabilized with the organotinthioalkonal composition of claim 1.

12. In a process for stabilizing an organotinthioalkanol stabilizer composition from gelation and precipitation, the improvement comprises the addition of:
0.1% to about 10% by weight of total stabilizer composition of bound chlorine and
about 0.1% to about 10% by weight of total stabilizer composition of a free mercaptan to the composition.

13. A process according to claim 12 employing about 0.1% to about 2.0% by weight of total stabilizer composition of bound chlorine and about 0.1 to about 5.0% by weight of total stabilizer composition of the free mercaptan.

14. A process according to claim 13 wherein the bound chlorine is incorporated into the composition by adding an organotin chloride or is present in the composition as an unreacted organotin chloride remaining after the formation of the organotinthioalkanol stabilizer.

15. A process according to claim 14 wherein the free mercaptan is selected from the group consisting of alkyl mercaptans, mercaptoacids, mercapto alkanols, mercaptoacid esters, mercaptoalkanol esters and mixtures thereof.

16. A process according to claim 15 wherein the organotin chloride comprises monobutyltin trichloride and the free mercaptan comprises 2-ethylhexyl mercapto acetate.

17. A process according to claim 15 wherein the bound chlorine is bonded to at least one of the tin of the organotinthioalkanol stabilizer, the tin of an organotin compound formed during the redistribution of the organotinthioalkanol and the tin of the organotin chloride, or the tin of the organotin chloride.

18. A process according to claim 12 wherein the organotinthioalkanol stabilizer composition has the NMR spectrum shown in the Figure.

19. An organotinthioalkanol-based stabilizer composition characterized by having been prepared by the process comprising the steps of:
adding an organotin chloride to the organotinthioalkanol stabilizer to produce 0.1% to about 10% by weight of the total stabilizer composition of bound chlorine and
adding about 0.1% to about 10% by weight of the total stabilizer composition of a free mercaptan selected from the group consisting of alkyl mercaptans, mercaptoacids, mercaptoalkanols, mercaptoacid esters, mercaptoalkanol esters and mixtures thereof.

20. A stabilizer composition according to claim 19 wherein the organotin chloride is added by allowing unreacted organotin chloride raw material used in the formation of the organotinthioalkanol to remain with the organotinthioalkanol stabilizer.

21. A stabilizer composition according to claim 19 wherein the organotin chloride is added neat after the formation of the organotinthioalkanol stabilizer.

22. A stabilizer composition according to claim 19 comprising about 0.1% to about 2.0% by weight of total stabilizer composition of bound chlorine and about 0.1% to about 5.0% by weight of total stabilizer composition of the free mercaptan.

23. An organotinthioalkanol stabilizer composition comprising:
at least one mercaptoalkanol residue bonded to a tin atom of the organotinthioalkanol through the sulfur atom of the residue;
at least 0.1% by weight of bound chlorine; and
at least 0.1% by weight of free mercaptan compound.

24. An organotinthioalkanol stabilizer composition according to claim 23 comprising:
about 3% to about 35% by weight of mercapto sulfur;
about 0.1% to about 10% by weight of bound chlorine;
about 0.1% to about 10% by weight of free mercaptan compound; and
about 16% to about 46% by weight of tin.

25. An organotinthioalkanol stabilizer composition according to claim 24 wherein about 3% to about 67% by weight of the organotinthioalkanol compound is the meraptoalkanol residue.

26. An organotinthioalkanol stabilizer composition according to claim 24 having:
about 0.1% to about 2.0% by weight of total stabilizer composition bound chlorine; and
about 0.1% to about 5.0% by weight of total stabilizer composition free mercaptan.

27. An organotinthioalkanol stabilizer composition according to claim 24 having the NMR spectrum shown in the Figure.

28. A resin composition comprising:
at least one vinyl halide resin and
the organotinthioalkanol stabilizer composition of claim 24.

29. A polyvinyl chloride pipe stabilized with the organotin thioalkanol compositon of claim 23.

30. A polyvinyl chloride injection molded article stabilized with the organotinthioalkanol composition of claim 23.

31. A polyvinyl chloride house siding product stabilized with the organotinthioalkanol compositon of claim 23.

* * * * *